US00PP10763P

United States Patent [19]

Didden

[11] Patent Number: Plant 10,763

[45] Date of Patent: Jan. 26, 1999

[54] POINSETTIA PLANT NAMED 'LIBERTY BRIGHT RED'

[75] Inventor: Frans Didden, Boskoop, Netherlands

[73] Assignee: Koninklijke Handelskwekerij Weduwe, P. Eveleens & Zonen B.V.-Royal Eveleens, Aalsmer, Netherlands

[21] Appl. No.: 842,081

[22] Filed: Apr. 28, 1997

[51] Int. Cl.[6] ..... A01H 5/00

[52] U.S. Cl. ..... Plt./86.4

[58] Field of Search ..... Plt./86.4

[56] References Cited

U.S. PATENT DOCUMENTS

P.P. 10,183 1/1998 Jacobsen ..... Plt./86.4

*Primary Examiner*—James R. Feyrer

*Attorney, Agent, or Firm*—C. A. Whealy

[57] ABSTRACT

A new and distinct cultivar of Poinsettia plant named 'Liberty Bright Red', characterized by its bright red bracts with pronounced lobing; bracts held horizontal or slightly upright; compact and uniform growth habit requiring few plant growth retardant applications; freely branching; dark green leaves with pronounced lobing; early flowering, short response time; and very good postproduction longevity.

3 Drawing Sheets

The present invention relates to a new and distinct cultivar of Poinsettia plant, botanically known as *Euphorbia pulcherrima* Willd., hereinafter referred to by the cultivar name Liberty Bright Red.

The new cultivar is a product of a mutation induction breeding program conducted by the inventor in Aalsmeer, The Netherlands. The objective of the breeding program was to develop compact poinsettia varieties that require few to no plant growth retardant applications and suitable for smaller containers; that flower early; have distinctively lobed leaves and flower bracts; and have desirable bract and leaf color.

The new cultivar is an induced mutation of the Poinsettia cultivar '490', disclosed in U.S. Plant Pat. No. 7,825. The new cultivar originated by exposing unrooted cuttings of the cultivar 490 to gamma radiation at a level of 2,500 rads eight times for a period of 15 minutes each. Following the radiation treatments, the cuttings were rooted and terminal apices were removed to promote lateral branch development. After lateral branches from the pinching reached sufficient size, terminal cuttings were harvested, planted and flowered in Aalsmeer, The Netherlands. The cultivar Liberty Bright Red was discovered and selected by the inventor as a single flowering plant within this population in Dec., 1994. The selection of this plant was based on its desirable bract color, early cyathia development and its distinct leaf and flower bract lobation patterns.

Asexual reproduction of the new cultivar by terminal cuttings taken at Aalsmeer, The Netherlands, has shown that the unique features of this new Poinsettia are stable and reproduced true to type in successive generations of asexual reproduction.

The following traits have been repeatedly observed and are determined to be the unique characteristics of 'Liberty Bright Red'. These characteristics in combination distinguish 'Liberty Bright Red' as a new and distinct cultivar:

1. Bright red bracts with pronounced lobing.
2. Bracts held horizontal or slightly upright.
3. Compact and unform growth habit requiring few plant growth retardant applications.
4. Freely branching.
5. Dark green leaves with pronounced lobing.
6. Early flowering, short response time.
7. Very good postproduction longevity.

The new cultivar can be compared to the parent cultivar 490. However in side-by-side comparisons conducted by the inventor in Aalsmeer, The Netherlands, plants of the new cultivar differs from plants of the cultivar 490 in the following characteristics:

1. Plants of the new Poinsettia have more pronounced lobing of the bracts compared to plants of the cultivar 490.
2. Bracts of the new Poinsettia are held more upright than bracts of the cultivar 490.
3. Bracts of the new Poinsettia are spaced closer together than bracts of the cultivar 490.
4. Cyathia of the new Poinsettia open earlier than cyathia of the cultivar 490.

The accompanying colored photographs illustrate the overall appearance of the new cultivar, showing the colors as true as it is reasonably possible to obtain in colored reproductions of this type.

The first photograph comprises a top perspective view of a typical potted plant of 'Liberty Bright Red'.

The second photograph comprises a close-up view of a typical inflorescence of 'Libery Bright Red'.

The third photograph comprises a top perspective view of upper (left) and lower (right) surfaces of typical bracts of 'Liberty Bright Red'.

The fourth photograph comprises a top perspective view of upper (left) and lower (right) surfaces of typical leaves of 'Liberty Bright Red'. Flower bract and foliage colors in the photographs may appear different from the actual colors due to light reflectance.

The cultivar Liberty Bright Red has not been observed under all possible environmental conditions. The phenotype may vary somewhat with variations in environment such as temperature, daylength and light intensity, without, however, any variance in genotype. The following observations, measurements and comparisons describe plants grown in Aalsmeer, The Netherlands, under commercial practice in a glass-covered greenhouse with temperatures of 20° to 21° C. initially, then decreasing to 14° C. as plants matured to improve the postproduction longevity. Short day treatments of 14 hours of dark were initiated two weeks after pinching to initiate flowering.

In the following description, color references are made to The Royal Horitcultural Society Colour Chart except where general terms of ordinary dictionary significance are used.

Classification:

*Botanical.*—*Euphorbia pulcherrima* Willd.

*Commercial.*—Poinsettia.

*Cultivar.*—'Liberty Bright Red'.

Parentage: Induced mutation of Poinsettia cultivar 490 disclosed in U.S. Plant Pat. No. 7,825.

Propagation:

*Type cutting.*—Terminal cuttings.

*Time to initiate roots.*—7 to 10 days at 21C.

*Rooting habit.*—Fine, freely branching.

Plant description:

*Plant form.*—Inverted triangle, top of plant rounded to flat.

*Growth habit.*—Freely branching and upright. Branching is enhanced by the removal of the apical shoot tip. Rapid growth rate, but low vigor. Relatively compact, best suited for 12.5 to 15-cm containers.

*Plant height.*—23 to 25 cm.

*Stem description.*—Diameter: 4 to 6 mm. Internode length: 3 to 5 cm. Color: Reddish.

*Foliage description.*—Arrangement: Opposite. Size: Length: 9 to 11 cm. Width: 6 to 7.5 cm. Petiole length: 4 to 6.5 cm. Shape: Broadly ovate. Tip: Acute. Base: Cuneate. Margin: Oak-leaf shape, pronounced lobing. Texture: Leathery. Color: Mature foliage upper surface: 137A/139A. Mature foliage lower surface: 137A/137B. Venation: Reddish. Petiole: Medium to dark red.

Inflorescence/flower description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under short day/long night conditions.

*Time to flower.*—Early flowering, about 7.5 weeks under short day/long night conditions.

*Inflorescence size.*—Diameter: About 23 cm. Height (depth): 1.5 to 2.5 cm.

*Flower bracts.*—Attitude: Horizontal to slightly upright, about 10° to stem axis. Quantity of flower bracts: 8 to 12 fully colored bracts per inflorescence, usually 1 or 2 green and red transitional bracts. Size: Length: 11 to 12 cm with petiole. Width: 8.5 to 10 cm. Shape: Broadly elliptic. Tip: Acute. Base: Cuneate. Margin: Immature: Entire. Mature: Oak-leaf shape, pronounced lobing. Texture: Not rugose between veins, smooth. Color: Mature, upper surface: 45A. Mature, lower surface: 53B. Venation, upper surface: 45A. Venation, lower surface: 53A.

*Cyathia.*—Quantity: About 9 per inflorescence. Diameter of cyathia cluster: 1.5 to 2 cm. Nectaries: Usually one and sometimes two per cyathium. Size: 3 to 4 mm. Color: Yellow, red margin not observed.

Disease resistance: No fungal, bacterial nor viral problems observed.

Postproduction longevity: Generally more than 3.5 weeks under interior conditions.

It is claimed:

1. A new and distinct cultivar of Poinsettia plant named 'Liberty Bright Red', as illustrated and described.

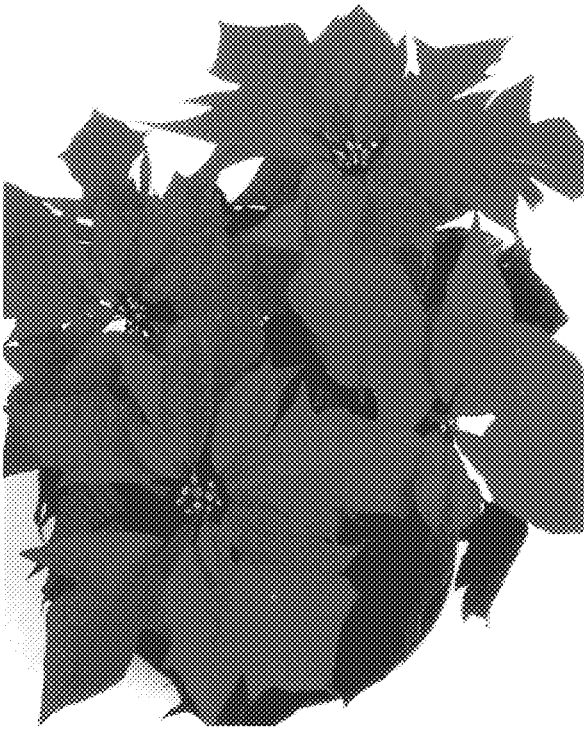

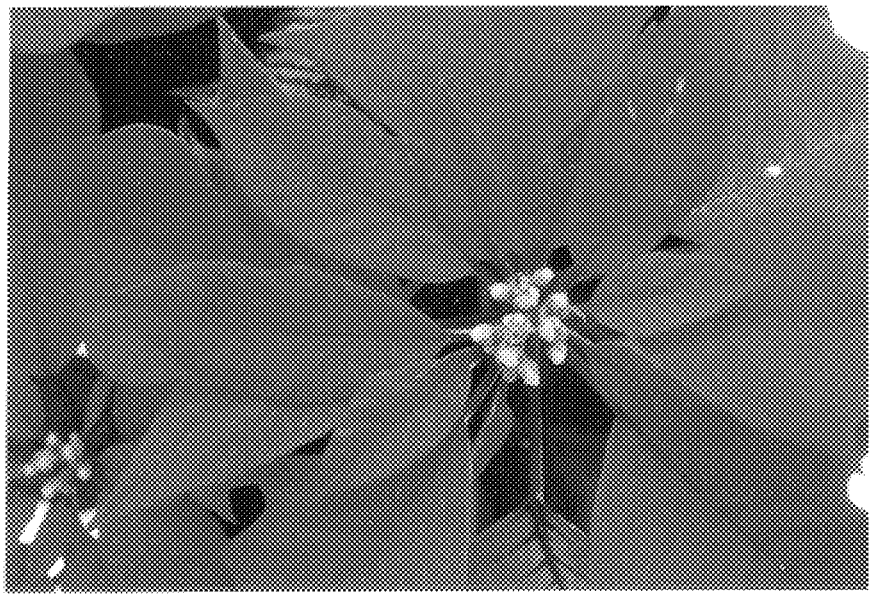

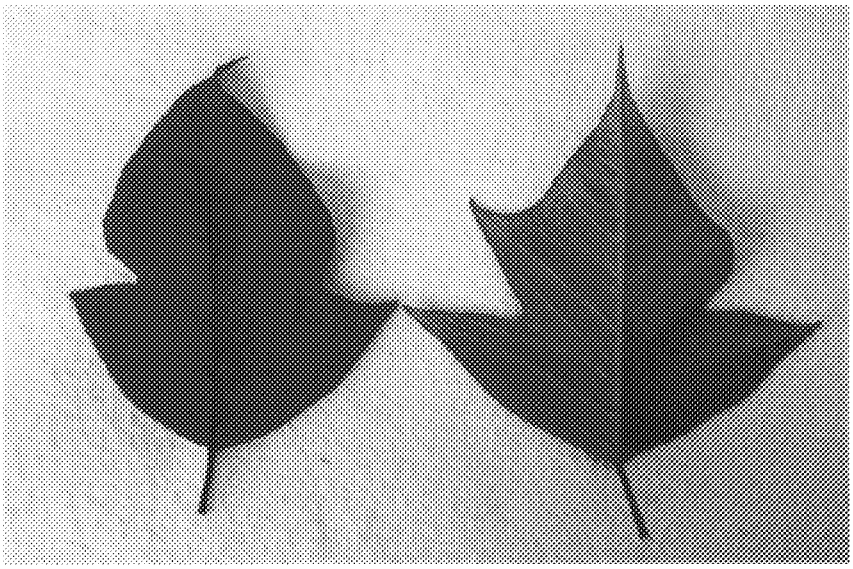
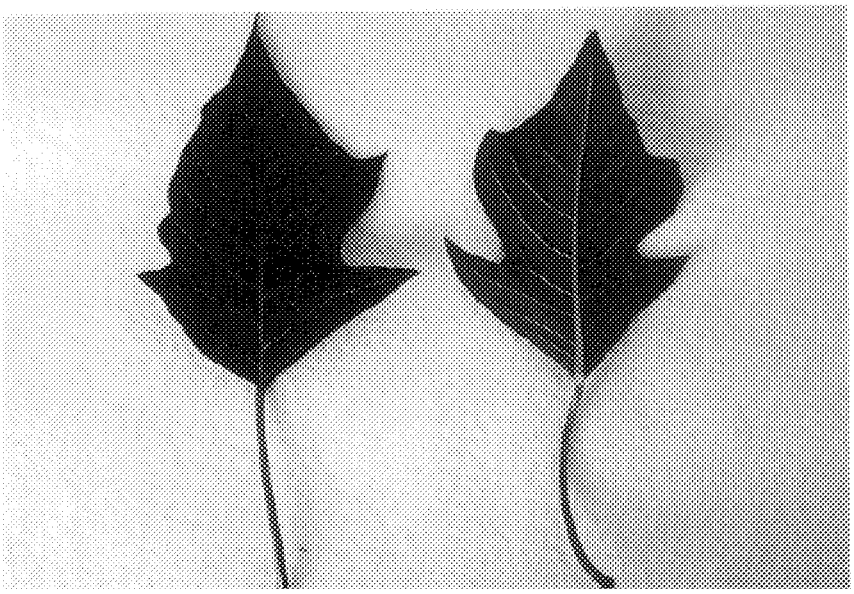

* * * * *